(12) United States Patent
Yang et al.

(10) Patent No.: US 12,311,389 B2
(45) Date of Patent: May 27, 2025

(54) MISTING NOZZLE AND SPRAY DEVICE

(71) Applicant: WUXI NEST BIOTECHNOLOGY CO, LTD, Jiangsu (CN)

(72) Inventors: Weidong Yang, Jiangsu (CN); Feng Chen, Jiangsu (CN); Xiaojian Zhu, Jiangsu (CN)

(73) Assignee: WUXI NEST BIOTECHNOLOGY CO, LTD, Wuxi (CN)

( * ) Notice: Subject to any disclaimer, the term of this patent is extended or adjusted under 35 U.S.C. 154(b) by 0 days.

(21) Appl. No.: 18/693,169

(22) PCT Filed: Jun. 2, 2023

(86) PCT No.: PCT/CN2023/098174
§ 371 (c)(1),
(2) Date: Mar. 19, 2024

(87) PCT Pub. No.: WO2024/212331
PCT Pub. Date: Oct. 17, 2024

(65) Prior Publication Data
US 2025/0128274 A1    Apr. 24, 2025

(30) Foreign Application Priority Data
Apr. 11, 2023  (CN) .......................... 202310376415.8

(51) Int. Cl.
*B05B 1/10*    (2006.01)
*A61M 11/00*    (2006.01)

(52) U.S. Cl.
CPC .............. *B05B 1/10* (2013.01); *A61M 11/007* (2014.02)

(58) Field of Classification Search
CPC ........... A61M 11/007; A61M 15/0001; A61M 15/08; B05B 1/10; B05B 11/02; B05B 11/007
See application file for complete search history.

(56) References Cited

U.S. PATENT DOCUMENTS

| 4,923,448 A * | 5/1990 | Ennis, III | B05B 1/3436 |
| | | | 128/200.22 |
| 7,182,277 B2 * | 2/2007 | Vedrine | B05B 11/0083 |
| | | | 239/533.1 |

(Continued)

FOREIGN PATENT DOCUMENTS

| CN | 102974012 A | 3/2013 |
| CN | 202777341 U | 3/2013 |

(Continued)

OTHER PUBLICATIONS

English translation for CN 110721373, machine translated by espacenet.com.*

(Continued)

*Primary Examiner* — Tu A Vo

(57) ABSTRACT

A misting nozzle and a spray device are provided. The misting nozzle includes a spray barrel body, a liquid guiding element disposed in the spray barrel body and including first and second blocking portions, and a liquid valve disposed inside the spray barrel body and abutting against the liquid guiding element. Herein, the spray barrel body has one end provided with an opening and other end axially tapering to define a liquid outlet. An outer circumference surface of the first blocking portion is provided with an axially extending liquid guiding groove. A gap is defined between the outer circumference surface of the second blocking portion and the inner wall of the spray barrel body. The outer circumference surface of the liquid valve abuts against the inner wall of the spray barrel body. The liquid valve is a resilient element provided with an axially extending groove.

18 Claims, 9 Drawing Sheets

(56) References Cited

U.S. PATENT DOCUMENTS

| | | | | |
|---|---|---|---|---|
| 8,276,581 B2* | 10/2012 | Kawamura | ......... | A61M 15/004 |
| | | | | 128/200.22 |
| 2017/0128364 A1* | 5/2017 | Kamishita | ............ | A61K 39/145 |

FOREIGN PATENT DOCUMENTS

| | | | | | |
|---|---|---|---|---|---|
| CN | 106178238 A | * | 12/2016 | | |
| CN | 106535969 A | | 3/2017 | | |
| CN | 107497036 A | * | 12/2017 | | |
| CN | 209512214 U | | 10/2019 | | |
| CN | 110721373 A | * | 1/2020 | .......... | A61M 11/007 |
| CN | 211798072 U | | 10/2020 | | |
| CN | 213058278 U | | 4/2021 | | |
| CN | 113797412 A | * | 12/2021 | | |
| WO | 2022026528 A1 | | 2/2022 | | |

OTHER PUBLICATIONS

Notice of Allowance of counterpart Chinese Patent Application No. 202310376415.8 issued on May 16, 2023.
First Search Report of counterpart Chinese Patent Application No. 202310376415.8 issued on May 12, 2023.

* cited by examiner

MISTING NOZZLE AND SPRAY DEVICE

TECHNICAL FIELD

The disclosure relates to the technical field of medical consumables, more particularly to a misting nozzle and a spray device.

BACKGROUND

Clinically, an administration method of spraying liquid to patients' affected areas or operative sites is usually used. For example, anesthetics may be administrated to mouths and noses, and medicaments may be sprayed to body parts including eyes, ears, noses, throats for treatment. Now, nasal spray vaccines are gradually widely used. The spraying administration has lots of advantages, such as no skin wound to worry about, and the elimination of a risk of non-sterile sharp things such as hypodermic injection needles for the medical care personnel. Usually, existing common spray devices for administration may consist of a spray head and a spray bottle or liquid reservoir which is matched and assembled therewith. The spray bottle usually contains dozens of doses. The spray head can be reused for repeatedly spraying. However, such spray devices cannot provide administration of precise dosing. Furthermore, as dozens of doses are stored in the spray bottle, there is a risk of administration of excessive doses.

In order to solve the problems of imprecise dosing and excessive storage in the spray bottle, a product has been provided, which has a hypodermic syringe barrel instead of the spray bottle. A barrel with an appropriate size may be selected depending on administration dosage, and administration dosage may be controlled according to graduations marked on the barrel. In existing mature technology of prefilled syringe for medication, the liquid medicament may be prefilled, and alternatively, the liquid medicament and the lyophilized powder may be prefilled in different chambers. However, the spray device for medicament administration which needs a syringe barrel for carrying or storing medicaments face new challenges. As medicament storage, transportation, and treatment before administration to users may be easily influenced by various environments, it is desired to provide a spray device for medicament administration with a sealing performance to ensure stability and sterility of the content.

SUMMARY

The invention aims to solve at least one of existing problems.

In order to achieve the above goal, the invention provides a misting nozzle, comprising:
  a spray barrel body having one end provided with an opening and other end tapering towards an axis thereof to define a liquid outlet;
  a liquid guiding element disposed in the spray barrel body and comprising a first blocking portion and a second blocking portion, wherein an outer circumference surface of the first blocking portion is provided in a direction of an axis thereof with a liquid guiding groove, the second blocking portion axially extends towards the liquid outlet, and a gap is defined between an outer circumference surface of the second blocking portion and an inner wall of the spray barrel body; and
  a liquid valve disposed inside the spray barrel body and abutting against the liquid guiding element, wherein an outer circumference surface of the liquid valve abuts against the inner wall of the spray barrel body, the liquid valve is provided in a direction of an axis with a groove, and the liquid valve is a resilient element.

Further preferably, the outer circumference surface of the liquid valve may be provided with a flange abutting against the inner wall of the spray barrel body, and the groove may be provided on the flange.

Further preferably, the liquid valve may have a columnar structure, and the groove may be provided on the outer circumference surface of the liquid valve.

Further preferably, a plurality of bosses may be provided inside the spray barrel body at positions corresponding to the liquid outlet, the plurality of bosses may be helically arranged about the liquid outlet with each two adjacent bosses defining a flow path, and an end of the second blocking portion away from the first blocking portion may abut against the bosses.

Further preferably, a swirling groove may be provided between the flow paths and the liquid outlet, and the swirling groove may have a cross section tapering in a direction from the flow paths to the liquid outlet.

Further preferably, an end of the first blocking portion away from the liquid outlet may be provided with a first abutment portion, and an end of the liquid valve facing the liquid guiding element may be provided with a second abutment portion abutting against the first abutment portion.

Further preferably, a radial width of the first abutment portion and/or the second abutment portion may be less than an inner diameter of the spray barrel body at a corresponding position, a first space may be defined between the first abutment portion and the inner wall of the spray barrel body, and between the second abutment portion and the inner wall of the spray barrel body, and the first space may be in communication with the liquid guiding groove and the groove, respectively.

Further preferably, a radial width of the second blocking portion may be less than a radial width of the first blocking portion, such that a step structure may be defined at a joint of the first blocking portion and the second blocking portion, a second space may be defined between the step structure and the inner wall of the spray barrel body, and the second space may be in communication with the liquid guiding groove.

Further preferably, the radial width of the second blocking portion may be less than the inner diameter of the spray barrel body at a corresponding position, such that a guiding gap communicating the second space and the flow paths may be defined between the outer circumference surface of the second blocking portion and the inner wall of the spray barrel body.

Further preferably, the liquid guiding element may be provided along an axis thereof with a central groove facing the liquid valve.

Further preferably, an end face of the liquid valve away from the liquid guiding element may be provided with a convex surface, and the convex surface may have a cross-section with contours defining an angle θ, wherein $100° \leq θ < 180°$.

A spray device is provided, which comprises a prefilled syringe and a misting nozzle as mentioned above.

The prefilled syringe comprises a syringe barrel, the liquid outlet end of the syringe barrel is sealed and disposed in the opening of the spray barrel body, and the liquid outlet end of the syringe barrel abuts against the liquid valve.

Compared with the existing technologies, the disclosure has advantages as follows.

The misting nozzle comprises the spray barrel body, in which the liquid guiding element and the liquid valve are disposed. Herein, the liquid valve is a resilient element, and the liquid valve and the liquid guiding element can get stuck inside the spray barrel body. Meanwhile, as the liquid guiding element and the liquid valve are respectively provided with the liquid guiding groove and the groove, the prefilled content can be conveyed through the opening of the spray barrel body to liquid outlet for misting. Furthermore, the liquid guiding element mainly functions to realize guiding and reduce dead volume of the misting nozzle. As the liquid guiding element takes up too much inner space of the spray barrel body, less volume of liquid would be remained in the spray barrel body, thereby reducing waste of the content.

A spray device comprises a syringe barrel which has the liquid outlet end abutting against the liquid valve, such that the liquid valve in the original state closes the liquid outlet end of the syringe barrel, and when the liquid valve is deformed, there is a gap for allowing the content to flow through, between the liquid valve and the liquid outlet end of the syringe barrel, to allow the content to flow through the groove of the liquid valve towards the liquid guiding element. Hence, the solution achieves good sealing effect, and ensures stability and sterility of the medicaments in the syringe barrel. It is safe to use and is convenient to operate.

Figure 1:
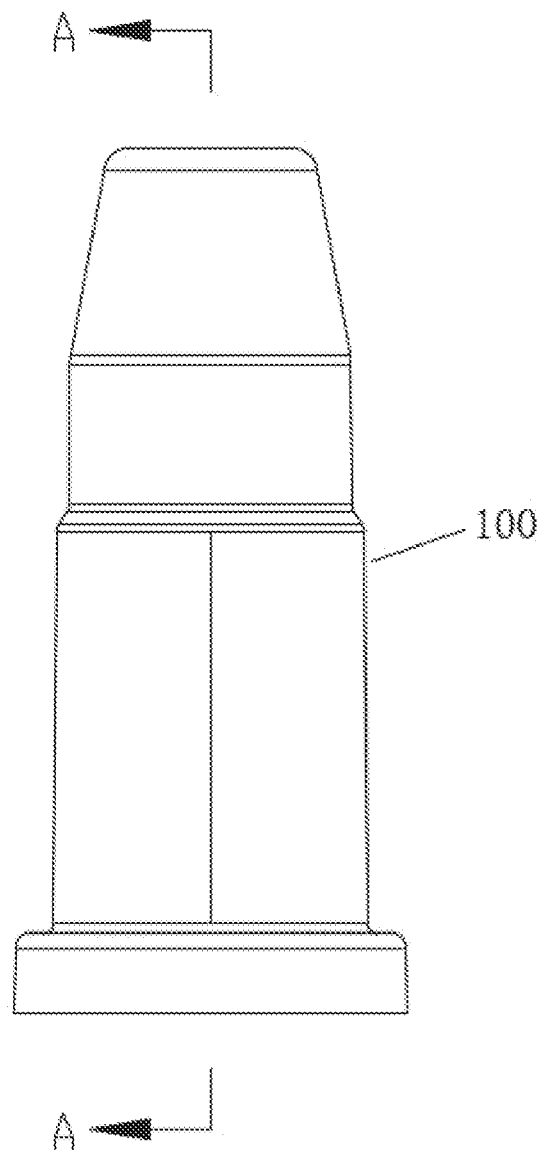
FIG. 1 is a schematic view of a misting nozzle of the disclosure.

In the drawings: 100. misting nozzle; 10. spray barrel body; 101. first cavity; 102. second cavity; 103. third cavity; 104. fourth cavity; 105. fifth cavity; 106. sixth cavity; 107. boss; 108. swirling groove; 109. liquid outlet; 110. first space; 111. second space; 112. guiding gap; 113. flow paths; 20. liquid guiding element; 201. first blocking portion; 202. second blocking portion; 203. first abutment portion; 204. central groove; 205. liquid guiding groove; 30. liquid valve; 301. flange; 302. convex surface; 303. second abutment portion; 304. groove; 200. prefilled syringe; 40. syringe barrel.

DETAILED DESCRIPTION OF ILLUSTRATED EMBODIMENTS

The invention will be further explained below in detail with reference to figures and embodiments. The embodiments are illustrative and are not intended to limit the scope.

It should be understood that the terms, such as "top", "bottom", "inner", "outer", "axial", "circumferential", "between", "close to", "away from", "one side/end", and "another side/end" as used in the description of the invention, refer to position and orientation relationships in accordance with drawings for convenience of description and for the purpose of simplicity. They are not intended to indicate or hint a limitation in terms of specific orientation or configuration and operation with specific orientation to the described device or element and should not be regarded as limiting.

The terms such as "first", "second" "fifth", and "sixth" are used for convenience of description and are not intended to indicate or imply relative importance. In addition, unless defined or specified otherwise, terms such as "mount", "connect" and "attach" used therein are intended to have meanings commonly understood in a broad sense. For example, "connect" may refer to fixedly connect, or detachably connect, or integrally connect; or mechanically connect, or electrically connect; or directly connect, or indirectly connect via an intermedium, or internally communicate between two components. The meanings of the terms used herein may be understood by those skilled in the art in accordance with specific conditions.

Embodiment 1

Figure 2:
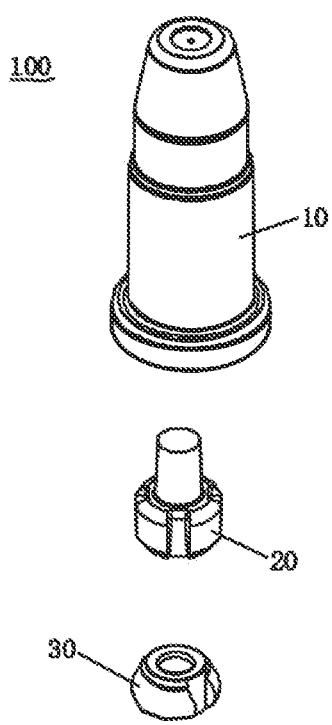
FIG. 2 is a schematic exploded view of a misting nozzle of the disclosure.

Referring to FIGS. 1-2, a misting nozzle is provided in the embodiment. The misting nozzle 100 comprises a spray barrel body 10, a liquid guiding element 20, and a liquid valve 30.

In some particular implementations, the spray barrel body 10 has a barrel shaped structure internally provided with a passage. One end of the spray barrel body 10 is provided with an opening, and the other end tapers in a direction of the axis of the spray barrel body 10 to define a liquid outlet 109, thereby allowing inside liquid to flow in a direction from the opening towards the liquid outlet 109. The liquid guiding element 20 and the liquid valve 30 may be placed in turn through the opening into the passage inside the spray barrel body 10.

In addition, the end of the spray barrel body 10 provided with the opening may be matched and attached to an end of a syringe, to facilitate the application of prefilling and sealing technology. It should be noted that, the prefilling and sealing technology has been commonly used in the biomedical field. The medical consumables may be prefilled with medicaments in the factory. In such a case, medicaments can be stored and transported in the medical consumables, and the medical consumables (fox example prefilled syringes) can be used for the administration of medicaments. The medicament prefilling procedure is usually performed in pharmaceutical factories or hospital pharmacies.

It should be noted that, in order to ensure stability and sterility of the content, the misting nozzle 100 in other implementations may comprise a cap (not shown in the drawings). The integral cap may have a cylindrical shaped structure. The end of the spray barrel body 10 provided with the liquid outlet 109 may be inserted into the cap. To some extent the cap has a protection function, and it prevents contaminants from passing through the liquid outlet 109 to enter the spray barrel body 10 and cause contamination and failure of the content. In order to facilitate operation and usage, the cap may be integrally removed from the spray barrel body 10 after assembly.

Figure 4:
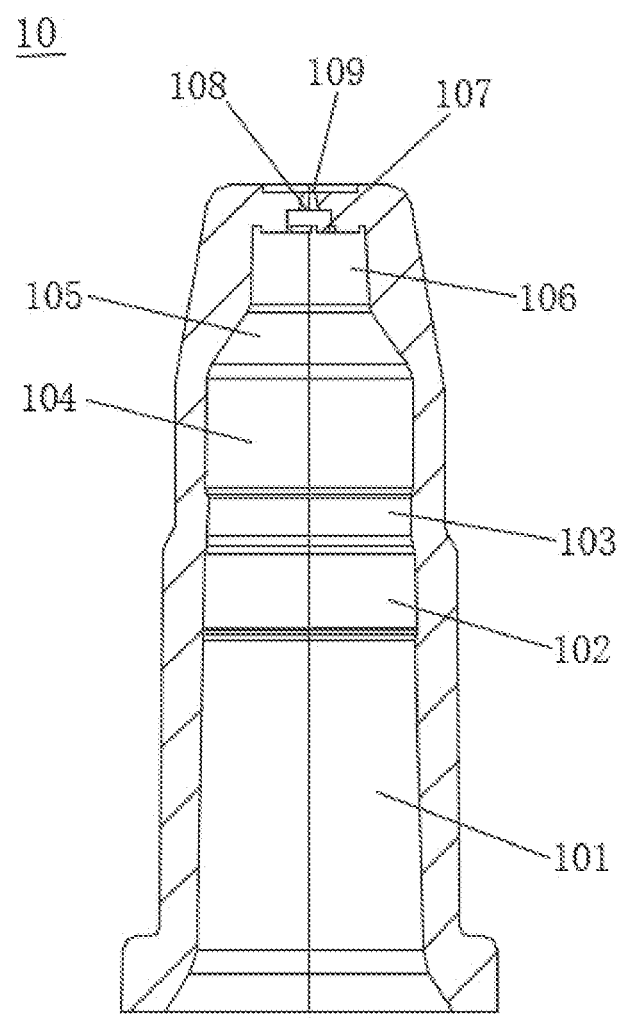
FIG. 4 is a cross-sectional view of a spray barrel body of the disclosure.

In some particular implementations, referring to FIG. 4, a first cavity 101, a second cavity 102, a third cavity 103, a fourth cavity 104, a fifth cavity 105, and a sixth cavity 106 may be defined inside the spray barrel body 10 in such an order in a direction from the end with the opening to the liquid outlet 109. Herein, the first cavity 101 serves to allow matching and attaching to an end of the syringe, the liquid guiding element 20 extends from the third cavity 103 to the sixth cavity 106, and the liquid valve 30 is placed within the second cavity 102 and the third cavity 103. It should be noted that a diameter of the third cavity 103 is less than a diameter of the second cavity 102, and a diameter of the sixth cavity 106 is less than a diameter of the fourth cavity 104. With the above structure, it facilitates mounting of the liquid guiding element 20 and the liquid valve 30.

Figure 3:
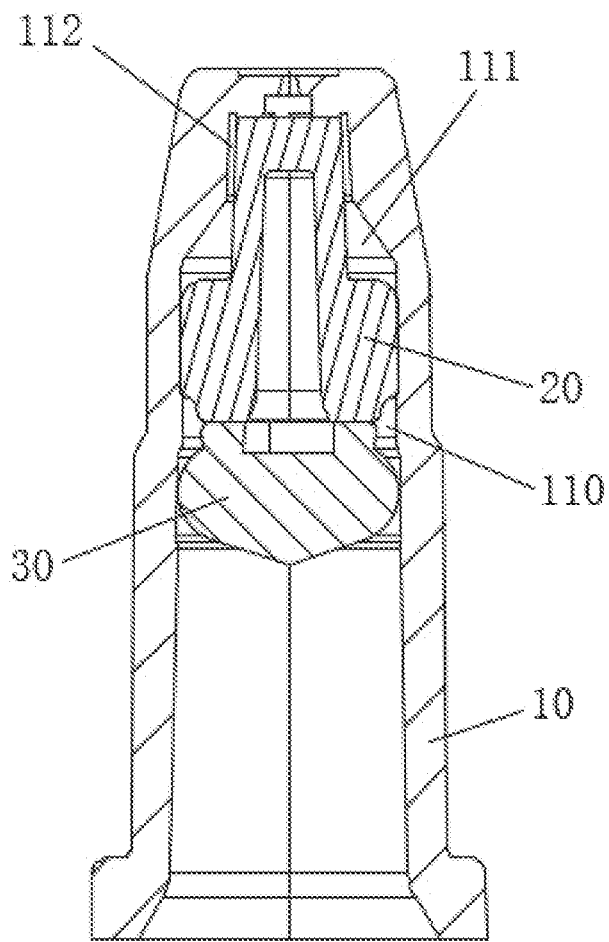
FIG. 3 is a cross-sectional view taken from A-A of FIG. 1 of the disclosure.
Figure 6:
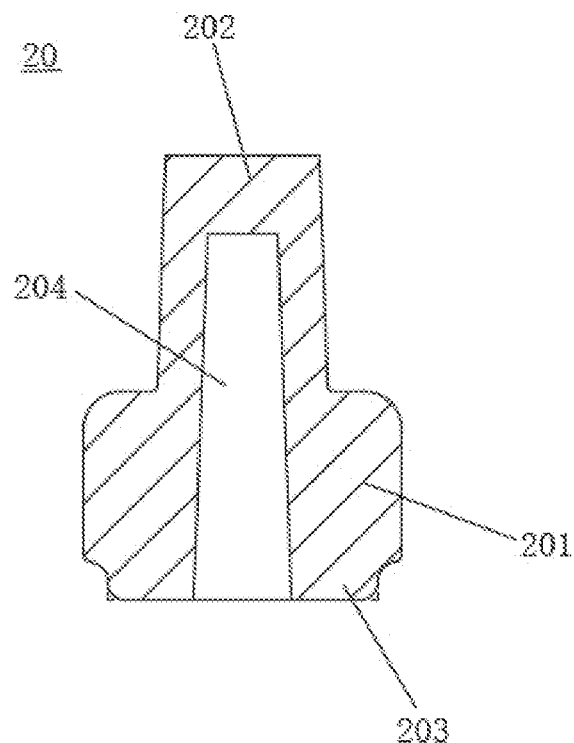
FIG. 6 is a cross-sectional view of a liquid guiding element of the disclosure.

In some particular implementations, referring to FIGS. 3 and 6, the liquid guiding element 20 comprises a first blocking portion 201 and a second blocking portion 202. The first blocking portion 201 is placed within the fourth cavity 104, and an outer circumference surface of the first blocking portion 201 is provided with at least one liquid guiding groove 205 extending in its axial direction. It should be noted that, the liquid guiding groove 205 may extend in a direction parallel to the axial direction of the spray barrel body 10. The liquid guiding groove 205 is in communication with the third cavity 103 and the fifth cavity 105, to facilitate liquid guiding of the content.

The liquid guiding element 20 mainly functions to realize guiding and reduce dead volume of the misting nozzle. In some implementations, the outer circumference surface of the first blocking portion 201 may abut against (interference fitting with) the inner wall of the spray barrel body 10. Consequently, the liquid guiding element 20 can be fixedly arranged inside the spray barrel body 10, such that the liquid guiding element is not easy to fall off from the spray barrel body 10. In such a case, the content can flow through the liquid guiding groove 205. In another implementation, a radial width of the first blocking portion 201 may be less than a radial width of the spray barrel body 10 at a corresponding position. That is, there is a gap between the first blocking portion 201 and the inner wall of the spray barrel body 10. Due to the liquid valve 30, the liquid guiding element 20 is limited at a position inside the spray barrel body 10. In such a case, the content can flow through both the gap and the liquid guiding groove 205.

In the above implementations, the first blocking portion 201 and the second blocking portion 202 may be integrally formed. The second blocking portion 202 extends along its axis from the end of the first blocking portion 201 towards the liquid outlet 109. In particular, the second blocking portion 202 may be placed in both the fifth cavity 105 and the sixth cavity 106. In order to allow the content to flow from the fifth cavity 105 to the liquid outlet 109, a gap is defined between the outer circumference surface of the second blocking portion 202 and the inner wall of the spray barrel body 10.

It should be noted that, the liquid guiding element 20 mainly functions to realize guiding and reduce dead volume of the spray barrel body 10 as mentioned above. Herein, the guiding function indicates that, the medicaments flowed through the liquid valve flows through the liquid guiding groove 205 and through the gap defined between the outer circumference surface of the second blocking portion 202 and the inner wall of the spray barrel body 10, to the liquid outlet 109, and then can be sprayed out from the liquid outlet 109. The reduction of dead volume indicates that, as the liquid guiding element 20 takes up too much inner space (the fourth, fifth, and sixth cavities) of the spray barrel body 10, less volume of liquid will be remained in the spray barrel body 10 after injection of the liquid medicaments in the syringe barrel, whereby waste of medicaments can be reduced.

Further preferably, the liquid guiding element 20 may be provided with a central groove 204 extending along its axis and facing the liquid valve 30. A cavity structure may be provided inside the liquid guiding element 20, and the opening of the cavity structure may be closed by the liquid valve 30, to prevent medicaments from entering the central groove 204. Due to the cavity structure of the liquid guiding element 20, it saves materials and thus the cost without affecting performance.

Figure 7:
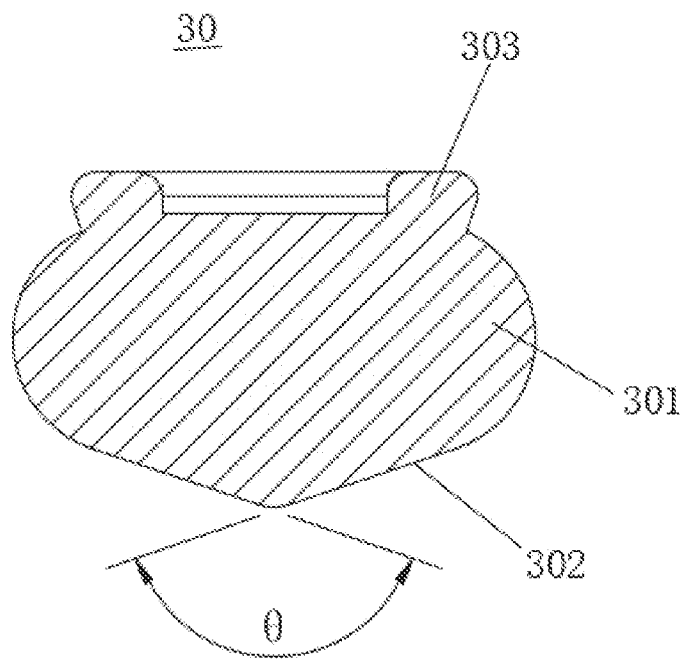
FIG. 7 is a cross-sectional view of a liquid valve of the disclosure.

In some particular implementations, referring to FIGS. 3 and 7, the liquid valve 30 is disposed inside the spray barrel body 10 and abuts against the liquid guiding element 20. A flange 301 may be provided on the outer circumference surface of the liquid valve 30. The flange 301 may abut against (interference fitting with) the inner wall of the spray barrel body 10 in such a manner that the flange 301 fits with the inner wall of the spray barrel body 10 and thus the liquid valve 30 is not easy to fall off from the spray barrel body 10. Consequently, the liquid valve 30 can be fixedly arranged inside the spray barrel body 10, and meanwhile it can axially limit the liquid guiding element 20. It ensures that the liquid guiding element 20 would not be displaced during transportation and usage, and thus ensures the spraying effect in subsequent use.

It should be noted that, the flange 301 may exactly fit with the inner wall of the spray barrel body 10, such that the liquid valve is not easy to fall out of the spray barrel body 10.

In addition, in order to allow the content to be introduced from the first cavity 101 to the third cavity 103, the flange 301 may be provided with at least one groove 304 extending in the axial direction of the liquid valve 30, at a position offset from the central portion of the liquid valve 30. The groove 304 may extend in a direction parallel to the axial direction of the spray barrel body 10.

Furthermore, the liquid valve 30 may be a resilient element which is deformable. The liquid valve 30 in the original state can exactly close a liquid outlet end of a syringe barrel. In a case that the liquid valve 30 is deformed, there is a gap between the liquid valve 30 and the liquid outlet end of the syringe barrel, allowing the liquid medicaments to flow through. The medicaments may be introduced through the groove 304 of the liquid valve 30 to third cavity 103, and then may be introduced to the liquid outlet 109 due to the liquid guiding element 20.

It should be noted that, the liquid valve 30 may return to the original state after deformation. To this end, the liquid valve 30 may be made of a material of any one of butyronitrile, silica gel, rubber, TPE, TPU, and PVC.

In other implementations, the flange 301 of the liquid valve 30 may be shaped to have a convex structure of hemisphere shape or cone shape.

In order to achieve a sealing between the syringe barrel and the liquid valve 30 which is a resilient element, in some particular implementations, the end face of the liquid valve 30 away from the liquid guiding element 20 may be provided with a convex surface 302. After prefilling, the convex surface 302, which is shaped to fit with and abut against the liquid outlet end of the syringe barrel, ensures that the liquid outlet end of the syringe barrel can be closed by the liquid valve 30 in the original state. In order to ensure stability and sterility of the medicaments in the syringe barrel to improve safety, the liquid valve 30 may be forced and deformed in a manner of applying a force on the convex surface 302 of the liquid valve 30. In such a case, the liquid at the liquid outlet end of the syringe barrel applies a force on the convex surface 302 when the liquid inside the syringe barrel is compressed, which results in an elastic deformation of the liquid valve 30 and allows the liquid inside the syringe barrel to flow into the third cavity 103 with the guiding of the groove 304.

It should be noted that, due to the arrangement of the convex surface 302 of the liquid valve 30, it is ensured that the medicaments flow in a single direction. It ensures a good sealing of the spray device before administration of medicaments to a patient, and prevents the medicaments from being contaminated by infectious microbes and the like. The liquid valve 30 may be forced to deform and allow the medicaments inside the syringe barrel to flow out only when a force is applied on the medicaments.

Referring to FIG. 7, the convex surface 302 in other implementations may have a cross-section with contours defining an angle θ, wherein 100°≤θ<180°, preferably the angle θ is 142°±37°.

In another implementation, the liquid valve 30 may have a columnar elastic structure, wherein the groove 304 is provided on the outer circumference surface of the liquid valve, and an end surface of the liquid valve 30 away from the liquid guiding element 20 may be a plane surface or a convex or concave surface for abutting, in an original state, against the liquid outlet end of the syringe barrel 40 to achieve sealing and for deforming, under the action of force, to define a path allowing the content to pass through.

In the above implementations, an end of the first blocking portion 201 away from the liquid outlet 109 is provided with a first abutment portion 203, an end of the liquid valve 30 facing the liquid guiding element 20 is provided with a second abutment portion 303 for abutting against the first abutment portion in such a manner that the liquid valve 30 closes the central groove 204 of the liquid guiding element 20 to prevent medicaments from entering the central groove 204. It lowers the cost of the liquid guiding element 20.

Figure 8:
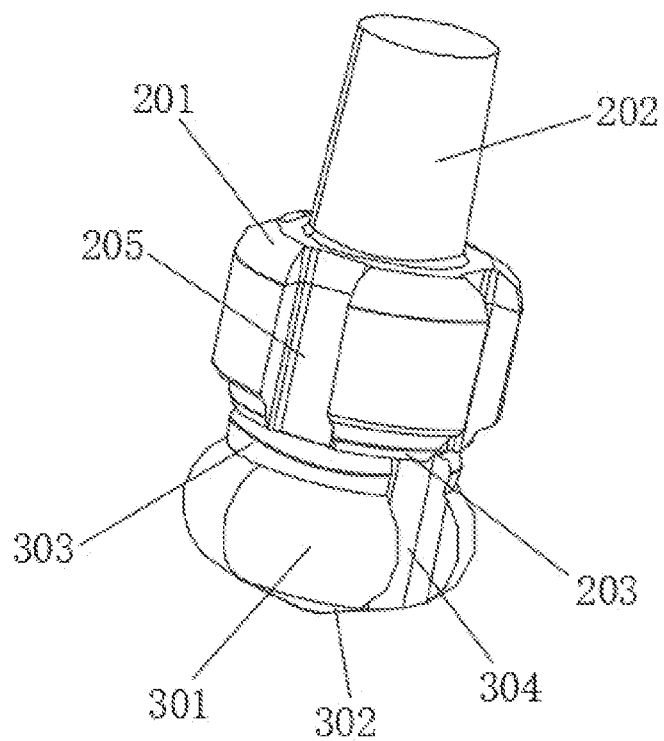
FIG. 8 is a structural view illustrating an assembly of a liquid guiding element and a liquid valve of the disclosure.

In the above implementations, radial widths of the first abutment portion 203 and the second abutment portion 303 are less than an inner diameter of the spray barrel body 10 at a corresponding position. A first space 110, which is annular, is defined between the first abutment portion 203 and the inner wall of the spray barrel body 10, and between the second abutment portion 303 and the inner wall of the spray barrel body 10. The first space 110 is in communication with the liquid guiding groove 205 and the groove 304, respectively. Referring to FIG. 8, during assembly, it does not need to place the liquid guiding element 20 and the liquid valve 30 at a specified position for alignment. That is, supplying of medicaments for administration does not require alignment of the liquid guiding groove 205 and the groove 304, thereby reducing requirements of assembly accuracy.

Further preferably, end surfaces of the first abutment portion 203 and the second abutment portion 303 engaged with each other may be plane surfaces. After close fit assembling, the assembly has further improved stability, preventing the medicaments from entering the central groove 204.

In other implementations, referring to FIG. 3, only one abutment surface is provided at one end of the liquid guiding element 20 close to the liquid valve 30, or at one end of the liquid valve 30 close to the liquid guiding element 20, with the purpose of defining an annular space between the outer wall of the liquid guiding element 20 or of the liquid valve 30 and the inner wall of the spray barrel body 10. The annular space may be in communication with the liquid guiding groove 205 and the groove 304, respectively. With such structure, during assembly, it similarly does not need to place the parts at a specified position for alignment, thereby reducing requirements of assembly accuracy.

In some particular implementations, the radial width of the second blocking portion 202 may be less than the radial width of the first blocking portion 201, such that a step structure is defined at a joint of the first blocking portion 201 and the second blocking portion 202. A second space 111 may be defined between the step structure and the inner wall of the spray barrel body 10. The second space 111 may be in communication with the liquid guiding groove 205, such that the medicaments in the first space 110 can flow to the second space 111 through the liquid guiding groove 205.

In some implementations, a guiding gap 112 may be defined between the outer circumference surface of the second blocking portion 202 and the inner wall of the spray barrel body 10, allowing medicaments to flow to the liquid outlet 109 through the guiding gap 112. Herein, in order to adapt to the shape of the inner space of the spray barrel body 10 and meanwhile reduce manufacturing difficulty and requirements of accuracy, it is conceivable to provide a second blocking portion 202 having a smooth outer wall without any liquid guiding groove. In such a case, a gap may be defined between the second blocking portion 202 and the inner wall of the spray barrel body 10, to allow the medicaments to pass through. The radial width of the second blocking portion 202 may be less than the inner diameter of the spray barrel body 10 at a corresponding position, to define the guiding gap 112.

Figure 5:
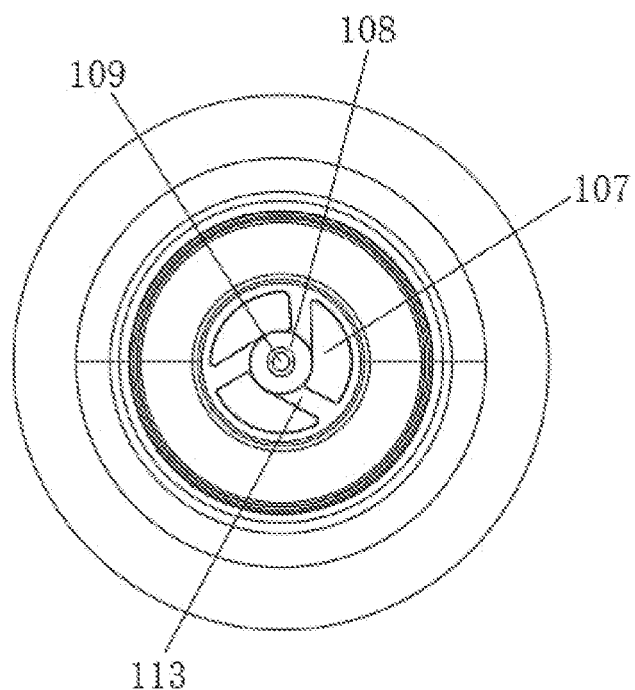
FIG. 5 is a bottom view of a spray barrel body of the disclosure.

In some particular implementations, referring to FIG. 5, a plurality of bosses 107 are provided inside the spray barrel body 10 at positions corresponding to the liquid outlet 109 in such a manner that the plurality of bosses 107 are helically arranged about a center, i.e., the liquid outlet 109, and flow paths 113 are respectively defined between each two adjacent bosses 107, and adjacent flow paths 113 form an angle. Herein, the guiding gap 112 is in communication with the second space 111 and the flow paths 113, to facilitate conveying of the medicaments to the liquid outlet 109.

In the implementation, the end of the second blocking portion 202 away from the first blocking portion 201 abuts against the boss 107, the end face of the second blocking portion 202 close to the liquid outlet 109 is an anvil face abutting against the bosses 107 which are helically arranged, thereby defining flow paths 113 between adjacent bosses 107.

In addition, a swirling groove 108 may be provided between the flow paths 113 and the liquid outlet 109, to allow the medicaments flowed from the flow paths 113 to converge into a helical flow. In order to ensure misting effect, it is conceivable that the swirling groove 108 may have a structure with a cross section tapering in a direction from the flow paths 113 to the liquid outlet 109. That is, the wall of the swirling groove 108 may have a step shape or cone shape in transverse direction, and the swirling groove 108 may have decreasing cross-sectional area. The helical flow may helically flow in the swirling groove 108 and become a mist getting out of the liquid outlet 109 due to release of pressure.

In other implementations, the liquid guiding element 20 and the spray barrel body 10 may be connected by snap connection or by connection of dispensing adhesive. The spray barrel body 10 may be provided in its inner wall with an annular protrusion, or a plurality of protrusions arranged annularly. In a case that the liquid guiding element 20 is placed in the spray barrel body 10, as the protrusion is located at a side of the liquid guiding element 20 close to the liquid valve 30, the liquid guiding element 20 will get stuck in the inner space of the spray barrel body 10 close to the liquid outlet 109 due to the protrusion. Alternatively, the liquid guiding element 20 may be fixed to the inner wall of the spray barrel body 10 by dispensing of adhesive.

In conclusion, inside the spray barrel body 10 in the embodiment, the liquid guiding element 20 and the liquid valve 30 are disposed. Herein, due to the flange 301 provided on the outer circumference surface of the liquid valve 30, the liquid valve 30 and the liquid guiding element 20 can be retained inside the spray barrel body 10. Meanwhile, as the liquid guiding element 20 and the liquid valve 30 are respectively provided with the liquid guiding groove 205 and the groove 304, the prefilled content can be conveyed through the opening of the spray barrel body 10 to liquid outlet 109 for misting. It reduces assembling difficulty and the requirement of accuracy. The conveying of medicaments does not require alignment of the groove 304 and the liquid guiding groove 205. In addition, the liquid guiding element 20 mainly functions to realize guiding and reduce dead volume of the misting nozzle. As the liquid guiding element 20 takes up too much inner space of the spray barrel body 10, less volume of liquid would be remained in the spray barrel body 10, thereby reducing waste of the content.

Embodiment 2

Figure 9:
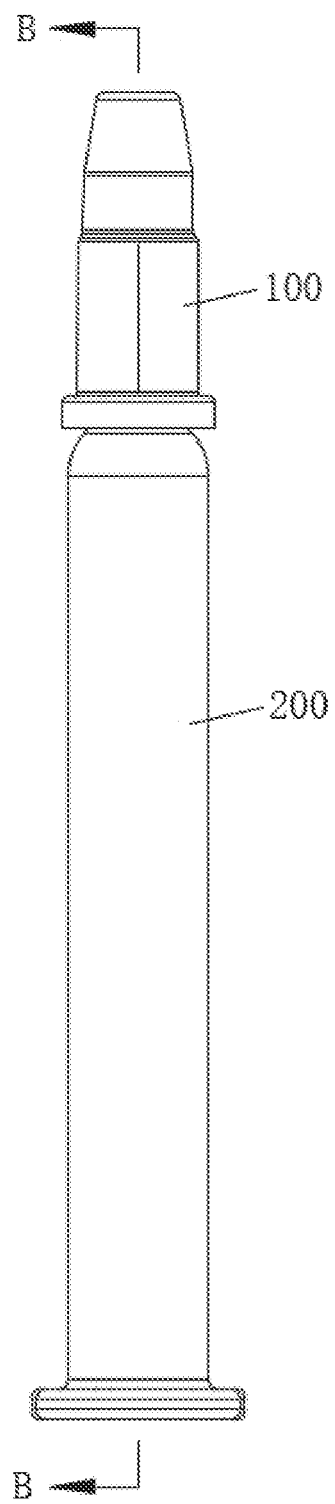
FIG. 9 is a schematic view of a spray device of the disclosure.
Figure 10:
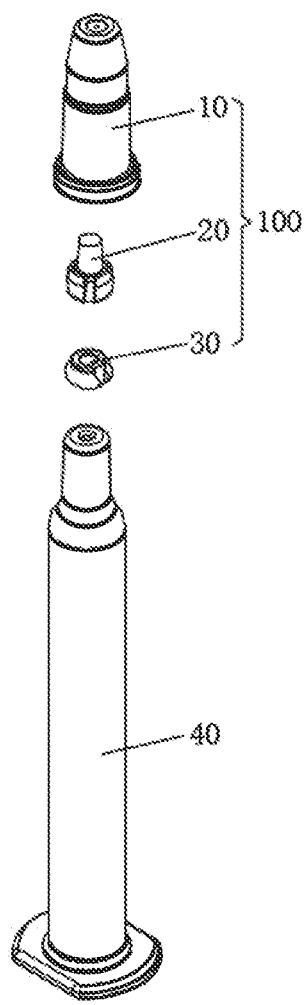
FIG. 10 is a schematic exploded view of a spray device of the disclosure.
Figure 11:
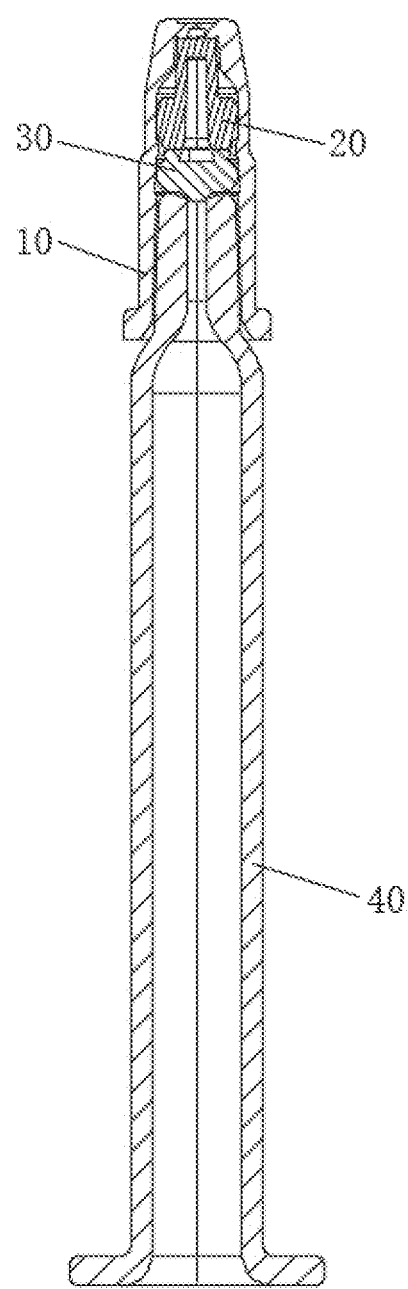
FIG. 11 is a cross-sectional view taken from B-B of FIG. 9 of the disclosure.

In conjunction to FIGS. 9-11, Embodiment 2 provides a spray device, which comprises a prefilled syringe and a misting nozzle according to Embodiment 1. Herein, the prefilled syringe comprises a syringe barrel 40, the liquid outlet end of the syringe barrel 40 is sealed and disposed in the opening of the spray barrel body 10 inside the first cavity 101 of the spray barrel body 10, and the liquid outlet end of the syringe barrel 40 abuts against the convex surface 302.

It should be noted that, the syringe barrel 40 has been provided in the art, which is internally arranged with a plunger. The plunger is mounted at an end with a plug which is slidable in the syringe barrel to achieve liquid sealing. When the plunger is pushed to force the liquid to flow to the liquid valve 30 and apply a force on the liquid valve 30, the liquid valve 30 under the action of force elastically deforms, to allow the medicaments inside the syringe barrel 40 to be conveyed into the first space 110 which is annular through the groove 304.

In other implementations, a portion of the plunger outward of the syringe barrel may be arranged with a dose limiter for limiting a length of the plunger moveable relative to the syringe barrel and thus limiting a dosage of medicaments which can be sprayed by the spray device in each spritz. When the limitation of the dose limiter on the plunger is released, the medicaments remained in the syringe barrel can be pushed out.

In other implementations, the liquid outlet end of the syringe barrel 40 and the spray barrel body 10 may be fixed with each other by snap connection. In an implementation, one of the outer wall of the liquid outlet end of the syringe barrel 40 and the inner wall of the spray barrel body 10 may be provided with an annular protrusion, and the other one may be provided with an annular groove. Alternatively, they may be fixed with each other by dispensing of adhesive. That is, the outer wall of the liquid outlet end of the syringe barrel 40 may be fixed to the inner wall of the spray barrel body 10 by adhesive.

In another implementation, the liquid valve 30 may have a columnar elastic structure, wherein the groove 304 is provided on the outer circumference surface of the liquid valve, i.e., at a position offset from the central portion of the liquid valve 30, and an end surface of the liquid valve 30 away from the liquid guiding element 20 may be a plane surface or a convex or concave surface for abutting, in an original state, against the liquid outlet end of the syringe barrel 40 to achieve sealing and for deforming, under the action of force, to define a path allowing the content to pass through.

In conclusion, the liquid outlet end of the syringe barrel 40 in the embodiment abuts against the convex surface 302 of the liquid valve 30, such that the liquid valve 30 in the original state closes the liquid outlet end of the syringe barrel 40, and when the liquid valve 30 is deformed, there is a gap between the liquid valve 30 and the liquid outlet end of the syringe barrel 40, allowing the content to flow through the groove 304 of the liquid valve 30 towards the liquid guiding element 20. Hence, the solution achieves good sealing effect, and ensures stability and sterility of the medicaments in the syringe barrel 40. It is safe to use and is convenient to operate.

All the above are merely some embodiments of the disclosure. It should be noted that those skilled in the art may obtain equivalents or modifications without departing from the principle of the disclosure. The invention is intended to cover all of the equivalents and modifications included. Basic principles, main features and advantages of the present disclosure are illustrated and described as above. Apparently, the above details of embodiments are not intended to limit the invention. The embodiments are exemplary rather than restrictive. The scope of the present invention is defined by the appended claims rather than the above description. Thus, the present invention is intended to cover all equivalents falling in the scope of the claims and modifications without departing from the principle of the disclosure.

In addition, it should be understood that, though the description is illustrated based on the above implementations, it is not intended to limit one independent technical solution in each implementation. The description is illustrated for the purpose of clarity. It should be understood that, the technical solutions of the above embodiments can be combined in any appropriate form by taking the specification as a whole by those skilled in the art, to obtain other implementations which can be appreciated by those skilled in the art.

The invention claimed is:

1. A misting nozzle comprising:
a spray barrel body having one end provided with an opening and a second end axially tapering to define a liquid outlet;
a liquid guiding element disposed in the spray barrel body and comprising a first blocking portion and a second blocking portion, wherein an outer circumference surface of the first blocking portion is provided with a liquid guiding groove extending axially, the second blocking portion axially extends towards the liquid outlet, and a gap is defined between an outer circumference surface of the second blocking portion and an inner wall of the spray barrel body; and a liquid valve disposed inside the spray barrel body and abutting against the liquid guiding element, wherein an outer circumference surface of the liquid valve abuts against the inner wall of the spray barrel body, the liquid valve is provided with a groove extending axially, and the liquid valve is a resilient element for abutting against a liquid outlet end of a syringe barrel in such a manner to close the liquid outlet end of the syringe barrel when the liquid valve is in an original state and define a gap between the liquid valve and the liquid outlet end of the syringe barrel to allow liquid medicaments to flow through when the liquid valve is elastically deformed; wherein the outer circumference surface of the liquid valve is provided with a flange abutting against the inner wall of the spray barrel body, and the groove of the liquid valve is provided on the flange; an end of the first blocking portion away from the liquid outlet is provided with a first abutment portion, and an end of the liquid valve facing the liquid guiding element is provided with a second abutment portion for abutting against the first abutment portion, so as to have the liquid guiding element configured to take up a volume of an inner space of the spray barrel body, thereby reducing a volume of liquid remained within the spray barrel body.

2. The misting nozzle according to claim 1, wherein the liquid valve has a columnar structure, and the groove of the liquid valve is provided on the outer circumference surface of the liquid valve.

3. The misting nozzle according to claim 2, wherein a plurality of bosses are provided inside the spray barrel body at positions corresponding to the liquid outlet, the plurality of bosses are helically arranged about the liquid outlet, the plurality of bosses define a plurality of flow paths, two adjacent bosses of the plurality of bosses define a flow path of the plurality of flow paths, and an end of the second blocking portion away from the first blocking portion abuts against the plurality of bosses.

4. The misting nozzle according to claim 3, wherein a swirling groove is provided between the flow paths and the liquid outlet, and the swirling groove have a cross section tapering in a direction from the flow paths to the liquid outlet.

5. A spray device comprising a prefilled syringe and the misting nozzle according to claim 4, wherein the prefilled syringe comprises the syringe barrel, the liquid outlet end of the syringe barrel is sealed and disposed in the opening of the spray barrel body, and the liquid outlet end of the syringe barrel abuts against the liquid valve.

6. The misting nozzle according to claim 3, wherein a radial width of the second blocking portion is less than a radial width of the first blocking portion, such that a step structure is defined at a joint of the first blocking portion and the second blocking portion, a second space is defined between the step structure and the inner wall of the spray barrel body, and the second space is in communication with the liquid guiding groove.

7. The misting nozzle according to claim 6, wherein the radial width of the second blocking portion is less than an inner diameter of the spray barrel body at a position corresponding to the second blocking portion, such that a guiding gap communicating the second space and the flow paths is defined between the outer circumference surface of the second blocking portion and the inner wall of the spray barrel body.

8. A spray device comprising a prefilled syringe and the misting nozzle according to claim 7, wherein the prefilled syringe comprises the syringe barrel, the liquid outlet end of the syringe barrel is sealed and disposed in the opening of the spray barrel body, and the liquid outlet end of the syringe barrel abuts against the liquid valve.

9. A spray device comprising a prefilled syringe and the misting nozzle according to claim 6, wherein the prefilled syringe comprises the syringe barrel, the liquid outlet end of the syringe barrel is sealed and disposed in the opening of the spray barrel body, and the liquid outlet end of the syringe barrel abuts against the liquid valve.

10. A spray device comprising a prefilled syringe and the misting nozzle according to claim 3, wherein the prefilled syringe comprises the syringe barrel, the liquid outlet end of the syringe barrel is sealed and disposed in the opening of the spray barrel body, and the liquid outlet end of the syringe barrel abuts against the liquid valve.

11. The misting nozzle according to claim 2, wherein an end face of the liquid valve away from the liquid guiding element is provided with a convex surface, and the convex surface has a cross-section with contours defining an angle $\theta$, wherein $100° \leq \theta < 180°$.

12. A spray device comprising a prefilled syringe and the misting nozzle according to claim 11, wherein the prefilled syringe comprises the syringe barrel, the liquid outlet end of the syringe barrel is sealed and disposed in the opening of the spray barrel body, and the liquid outlet end of the syringe barrel abuts against the liquid valve.

13. A spray device comprising a prefilled syringe and the misting nozzle according to claim 2, wherein the prefilled syringe comprises the syringe barrel, the liquid outlet end of the syringe barrel is sealed and disposed in the opening of the spray barrel body, and the liquid outlet end of the syringe barrel abuts against the liquid valve.

14. The misting nozzle according to claim 1, wherein a radial width of the first abutment portion and/or the second abutment portion is less than an inner diameter of the spray barrel body at a position corresponding to the first abutment portion and/or the second abutment portion, a first space respectively in communication with the liquid guiding groove and the groove of the liquid valve is defined between the first abutment portion and the inner wall of the spray barrel body, and between the second abutment portion and the inner wall of the spray barrel body.

15. A spray device comprising a prefilled syringe and the misting nozzle according to claim 14, wherein the prefilled syringe comprises the syringe barrel, the liquid outlet end of the syringe barrel is sealed and disposed in the opening of the spray barrel body, and the liquid outlet end of the syringe barrel abuts against the liquid valve.

16. The misting nozzle according to claim 1, wherein the liquid guiding element is provided along an axis thereof with a central groove facing the liquid valve.

17. A spray device comprising a prefilled syringe and the misting nozzle according to claim 16, wherein the prefilled syringe comprises the syringe barrel, the liquid outlet end of the syringe barrel is sealed and disposed in the opening of the spray barrel body, and the liquid outlet end of the syringe barrel abuts against the liquid valve.

18. A spray device comprising a prefilled syringe and the misting nozzle according to claim 1, wherein the prefilled syringe comprises the syringe barrel, the liquid outlet end of the syringe barrel is sealed and disposed in the opening of the spray barrel body, and the liquid outlet end of the syringe barrel abuts against the liquid valve.

* * * * *